April 14, 1970 R. S. MOORE Plant Pat. 2,967
MINIATURE ROSE PLANT
Filed April 15, 1968
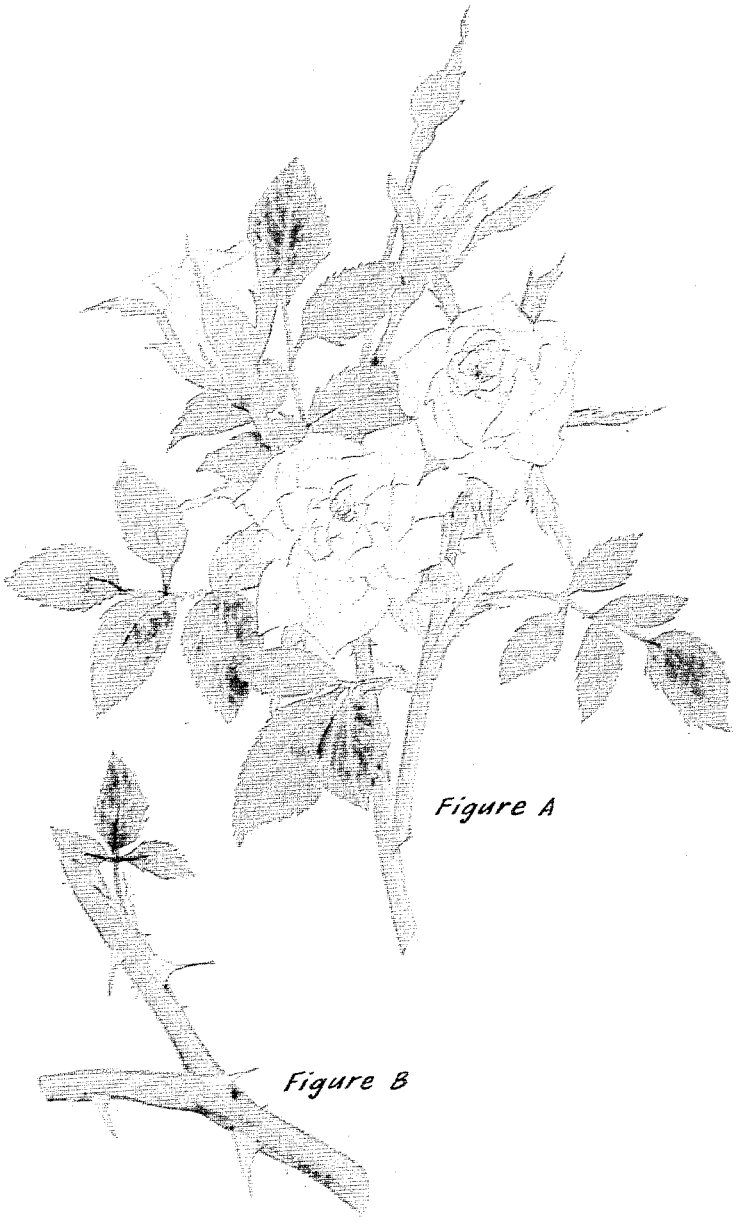
Figure A
Figure B
WITNESS
Jeanette Nunn Copley
INVENTOR
RALPH S. MOORE

United States Patent Office

Plant Pat. 2,967
Patented Apr. 14, 1970

2,967

MINIATURE ROSE PLANT

Ralph S. Moore, 2519 E. Noble Ave.,
Visalia, Calif. 93277

Filed Apr. 15, 1968, Ser. No. 721,533
Int. Cl. A01h 5/02
U.S. Cl. Plt.—7 1 Claim The present invention relates to a new and distinct variety of hardy, dwarf, bush type rose plant of the miniature class; the variety being primarily characterized —as to novelty—by buds and flowers of soft to medium pink color blended with shades of yellow.

The variety is further characterized by:

An abundance of bloom, with flowers borne singly or several to the stem.

Moderate fragrance.

A plant which is vigorous, of rounded to spreading habit, and with semi-glossy, medium small foilage with pointed leaflets; the buds and flowers being similar in size and shape, as compared to Easter Morning (United States Plant Patent No. 2,177) but with a blending of pink shades instead of white. The plant which has a normal height of 10" to 14" at maturity can easily be maintained at 10" or less with occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located as Visalia, Calif., under conditions of careful control and observation, as a cross between Golden Glow, a climber (United States Plant Patent No. 263, expired), as the seed parent, and Little Buckaroo (United States Plant Patent No. 1,726) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; garden decoration; potted plant.

Class: Miniature.

Flowers:

*Continuity.*—Continuous; repeat-blooms all season.

*Fragrance.*—Slight to moderate—sweet; tea rose.

Flowers borne: Singly and several together on 3" to 4"; sturdy, wire-like stem.

Quantity of bloom: Average abundance both outside and in greenhouse.

Bud:

*Peduncle.*—Medium length; erect; light green; with moderate number of short stiff hairs or prickles.

*Before calyx breaks.*—Size, small.

*Form.*—Short pointed; with foliaceous appendages and few or no hairs on surface of bud; with foliaceous parts extending beyond the tip of the bud equal to one half or more of its length.

*Color.*—Medium green, sometimes tinted reddish or bronze.

*As calyx breaks.*—Color: medium red; size—small.

*Form.*—Short pointed, becoming short urn-shaped as it opens.

*Opening.*—Usually opens well in all weather.

Bloom:

*Size when fully open.*—Small, averaging 1⅛" to 1⅜".

*Petalage.*—Very double—50 or more petals (usually with an additional 10–20 very small petals or petaloids), arranged regularly.

*Form.*—Flat or slightly rounded (high center) at first with petals rolled loosely outward, and later at maturity remaining loosely rolled outward with outer petals rolled more downward to give a more or less ball effect.

Petals: Rather thick; stiff; satiny both inside and outside. Shape: outside petals—broad lanceolate with round tip; intermediate petals—broad lanceolate, rounded with short acute tip; inside petals—narrow lanceolate, acute tip.

Color: Newly opened flower from a plant grown indoors in plastic greenhouse (April 1967) Visalia, Calif.

*Outside petal.*—Outside surface—light Rose Pink 427/2 to Rose Pink 427/3 shading into pale pinkish-yellow thence to pale yellow or greenish-yellow at base; inside surface—Rose Pink 427 shading into pale yellow/pink thence to pale yellow at base.

*Intermediate petal.*—Outside surface—Rose Pink 427/3 shading to pale yellow/pink thence into pale yellow at base; inside surface—Rose Pink 427/2 fading to pale yellow/pink, thence into yellow at base.

*Inside petal.*—Outside surface—Rose Pink 427/3 on outer one fourth blending into soft yellow/pink, thence to yellow at base; inside surface—Rose Pink 427/3 on tip blending into pale yellow/pink thence to bright yellow at base.

*General color effect newly opened flower.*—Soft pink with coral and/or peach shadings; outer petals tipped deeper shades of rose pink. As flowers age petals become almost red, especially outdoors in cool weather.

*Behaviour.*—Spent blooms may persist for a time as flower ages, then petals usually drop clean.

*Flower longevity (April 1968).*—Bush in pot in greenhouse—5 to 8 days. Cut flowers at living room temperature—4 to 7 days.

Reproductive organs:

*Stamens.*—Average number; arranged irregularly about pistil.

*Filaments.*—Short; of varying length.

*Pollen.*—Small amount; yellow.

*Pistils.*—Average.

*Styles.*—Medium length; bunched; pale greenish color.

*Stigma.*—Pale, greenish-white.

*Ovaries.*—All enclosed in calyx.

*Hips.*—Rare; small; round.

*Sepals.*—Permanent; spear shaped.

*Seeds.*—Rare; not viable.

Foliage:

*Leaves.*—Compound of five leaflets (occasionally 3); abundant; medium small (similar to Little Buckaroo); leathery; semi-glossy.

*Leaflets.*—Shape—broad lanceolate; apex acute; base nearly round; margin serrate. Color—normal green; new growth sometimes tinted bronze. Rachis—medium strength; upper side grooved; under side sparsely to moderately thorny. Stipules—medium to long; medium width; short to medium length points, turned out at an angle of 45 degrees or less.

Growth:

*Habit.*—dwarf; bushy; rounded to spreading (outdoors); much branched.

*Growth.*—Free; vigorous.

*Canes.*—Medium; slender.

*Main stems.*—Color—medium green. Thorns—moderately thorny; long oval base; medium length; hooked very slightly downward; color—gray or light brownish-gray. Prickles—none. Hairs—none.

*Branches.*—Color—medium green. Thorns—moderately throny; medium length; hooked slightly downward; medium to long oval base. Prickles—none. Hairs—none.

*New shoots.*—Color—medium waxy green; sometimes tinted bronze. Thorns—moderately thorny; medium length; hooked slightly downward; light brown, sometimes tinted pink or greenish; sharp points; base—short, oval. Prickles—none. Hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers resembling the Easter Morning miniature rose (U.S. Plant Patent No. 2,177) in general form and the flouribunda rose Pinocchio (U.S. Patent No. 484, expired) in color, the general color effect of the freshly opened flower being soft to medium pink, becoming deeper pink as flower ages; and further characterized by a plant which is vigorous and compact in growth, each to propagate from cuttings, with medium small semi-glossy foliage and an abundance of bloom borne almost continuously throughout the growing season with flowers borne singly or several to stem.

No references cited.

ROBERT E. BAGWILL, Primary Examiner